US012766029B2

(12) United States Patent
McGregor et al.

(10) Patent No.: US 12,766,029 B2
(45) Date of Patent: Oct. 20, 2026

(54) CLINICAL GARMENT WITH INSULATION

(71) Applicant: Solventum Intellectual Properties Company, Maplewood, MN (US)

(72) Inventors: Andrew J. McGregor, West Lakeland, MN (US); John R. Stark, St. Paul, MN (US); James A. Thielen, Hugo, MN (US); Jenna L. Lindsay, Woodbury, MN (US); Daniel P. Doran, Minneapolis, MN (US); Amanda M. Rue, St. Paul, MN (US); Benjamin C. Stanaway, St. Paul, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 987 days.

(21) Appl. No.: 17/621,365

(22) PCT Filed: Jun. 26, 2020

(86) PCT No.: PCT/IB2020/056077
§ 371 (c)(1),
(2) Date: Dec. 21, 2021

(87) PCT Pub. No.: WO2020/261211
PCT Pub. Date: Dec. 30, 2020

(65) Prior Publication Data

US 2022/0354690 A1 Nov. 10, 2022

Related U.S. Application Data

(60) Provisional application No. 62/866,688, filed on Jun. 26, 2019.

(51) Int. Cl.
*A41D 27/04* (2006.01)
*A41D 13/12* (2006.01)
(Continued)

(52) U.S. Cl.
CPC ............ *A61F 7/02* (2013.01); *A41D 13/1245* (2013.01); *A41D 27/04* (2013.01); *A61F 7/0085* (2013.01);
(Continued)

(58) Field of Classification Search
CPC .... A61F 7/02; A61F 7/0085; A61F 2007/006; A61F 2007/0091; A61F 2007/0233;
(Continued)

(56) References Cited

U.S. PATENT DOCUMENTS 4,118,531 A 10/1978 Hauser
4,685,155 A 8/1987 Fingerhut et al.
(Continued)

FOREIGN PATENT DOCUMENTS

CN 206964075 2/2018
EP 0389561 10/1995
(Continued)

OTHER PUBLICATIONS

Www.3m.com. [Online]. Available: https://www.3m.com/3M/en_US/thinsulate-us/technical-data-sheets/. (Year: 2016).*
(Continued)

*Primary Examiner* — Joanne M Rodden
*Assistant Examiner* — Dana Stumpfoll

(57) ABSTRACT

Aspects of the present disclosure can be related to a warming device, systems, and methods of using. The warming device can include a clinical garment comprising a body portion adapted to cover a portion of a patient, an inner surface configured to face the patient, and an outer surface opposite the inner surface. The body portion can include sleeves sized and positioned for receiving the patients arms. In addition, the clinical garment can include an insulative layer comprising an insulative edge portion disposed on the clinical
(Continued)

garment. The insulative edge portion is configured to make the warming device non-linting.

19 Claims, 11 Drawing Sheets

(51) Int. Cl.
*A61F 7/00* (2006.01)
*A61F 7/02* (2006.01)

(52) U.S. Cl.
CPC . *A61F 2007/006* (2013.01); *A61F 2007/0091* (2013.01); *A61F 2007/0233* (2013.01); *A61F 2007/0234* (2013.01); *A61F 2007/0249* (2013.01); *A61F 2007/0255* (2013.01); *A61F 2007/0257* (2013.01); *A61F 2007/0258* (2013.01)

(58) Field of Classification Search
CPC ...... A61F 2007/0234; A61F 2007/0249; A61F 2007/0255; A61F 2007/0257; A61F 2007/0258; A41D 13/1245; A41D 27/04
See application file for complete search history.

(56) References Cited

U.S. PATENT DOCUMENTS

| | | | |
|---|---|---|---|
| 5,148,002 A | 9/1992 | Kuo et al. | |
| 5,891,187 A | 4/1999 | Winthrop | |
| 5,997,572 A | 12/1999 | Arnold | |
| 6,245,096 B1 | 6/2001 | Tomic-Edgar | |
| 7,862,599 B2 | 1/2011 | Anderson | |
| 9,956,112 B2 * | 5/2018 | van Oudenallen | A61F 7/0085 |
| 2004/0040087 A1 * | 3/2004 | Lack | A47G 9/086 5/413 R |
| 2006/0247745 A1 | 11/2006 | Thompson | |
| 2007/0093882 A1 * | 4/2007 | Anderson | A61F 7/00 607/104 |
| 2010/0269241 A1 | 10/2010 | Baychar | |
| 2011/0119811 A1 | 5/2011 | Rock et al. | |
| 2012/0047623 A1 | 3/2012 | van Oudenallen | |
| 2012/0305541 A1 * | 12/2012 | Giles | A41D 13/0051 2/114 |
| 2014/0058485 A1 * | 2/2014 | Augustine | A61F 7/0085 607/107 |
| 2015/0335470 A1 * | 11/2015 | Panser | A41D 13/0051 607/107 |
| 2015/0366273 A1 * | 12/2015 | Rudick | A41D 13/0012 2/94 |
| 2015/0374048 A1 | 12/2015 | Theodossiou | |
| 2017/0313021 A1 * | 11/2017 | Chakravarty | B32B 27/308 |
| 2018/0098584 A1 | 4/2018 | Pezzimenti et al. | |
| 2019/0110615 A1 | 4/2019 | Vergona | |
| 2019/0240066 A1 * | 8/2019 | Hood | A61F 7/02 |

FOREIGN PATENT DOCUMENTS

| | | |
|---|---|---|
| EP | 0389561 B1 | 10/1995 |
| EP | 1937196 | 2/2013 |
| EP | 2611399 A1 | 7/2013 |
| EP | 2611399 | 7/2015 |
| JP | 2017-141517 | 8/2017 |
| JP | 2017153906 A | 9/2017 |
| WO | WO 2001-017470 | 3/2001 |
| WO | WO 2006-076148 | 7/2006 |
| WO | WO 2006-086587 | 8/2006 |
| WO | WO 2007-047917 | 4/2007 |
| WO | WO 2011-049744 | 4/2011 |
| WO | 2012028603 A1 | 3/2012 |
| WO | WO 2014-092874 | 6/2014 |
| WO | WO 2014-180975 | 11/2014 |
| WO | WO 2016-105461 | 6/2016 |
| WO | WO 2016-105462 | 6/2016 |
| WO | WO 2016-105475 | 6/2016 |
| WO | 2020261186 A1 | 12/2020 |
| WO | 2020261211 A1 | 12/2020 |
| WO | WO 2020-261212 | 12/2020 |

OTHER PUBLICATIONS

Www.3m.com.[Online].Available:https:/Avwww.3m.com/3M/en_US/thinsulate-US/technical-data-sheets/. (Year: 2016).*
3M, "Technical Data Sheet Typical Values, 3M (TM) Thinsulate (TM) Insulation (Types U/US/UDS) Product Designation Basis Weight", Aug. 1, 2016, 4 pages, XP055729766.
Fanger, "Thermal Comfort: Analysis and Applications in Environmental Engineering", Danish Technical Press, 1970, pp. 5-67.
International Search Report for PCT Application No. PCT/IB2020/056040, mailed on Sep. 17, 2020, 7 pages.
International Search Report for PCT Application No. PCT/IB2020/056077, mailed on Sep. 23, 2020, 8 pages.
International Search Report for PCT Application No. PCT/IB2020/056078, mailed on Sep. 23, 2020, 8 pages.
3M, "Technical Data Sheet—Type U Original," Thinsulate (TM) Insulation (Types U/US/UDS) Product Designation Basis Weight, Aug. 2016, 4 pages.

* cited by examiner

CLINICAL GARMENT WITH INSULATION

CROSS REFERENCE TO RELATED APPLICATIONS

This application is a national stage filing under 35 U.S.C. 371 of PCT/IB2020/056077, filed Jun. 26, 2020, which claims the benefit of U.S. Provisional Patent Application No. 62/866,688, filed Jun. 26, 2019, the disclosure of which are incorporated by reference in their entirety herein.

BACKGROUND

Pneumatic devices which transfer heat between thermally-conditioned air and a body are known. For example, there are inflatable pneumatic devices that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These inflatable devices are typically characterized as "blankets" or "covers". 3M makes and sells such devices under the BAIR HUGGER trade designation. One such device is the Model 622 Blanket.

Inflatable pneumatic warming blanket or cover devices are adapted especially for use with supine persons and are typically deployed by being laid directly on a person lying on a bed, a gurney, or a surgery platform, so as to drape over or cover some portion of the person. Because these devices are designed to cover and hang about or over a supine person, they are not easily or readily deployed on persons who are standing, sitting, reclining or moving. In particular, inflatable blankets are not suitable in a clinical setting in which it is desirable to warm a patient, and also necessary that the patient be able to move about and between various postures. In addition, there are a variety of clinical settings in which patient warming is desirable, with each setting requiring its own unique access to patient anatomy that may not be afforded by an inflatable blanket. For example, examination or treatment of a patient in a primary anesthesia care unit (PACU) could call for access to patient lines in the chest area, setting IV's in the arm, application of a stethoscope to the back and/or side, or application of a blood pressure cuff. Further, patient mobility throughout a clinic, nursing home, hospice care, or a hospital is highly desirable, but would be severely curtailed with use of inflatable blankets. For example, transporting a patient to an x-ray or MRI location in a wheelchair, would be made problematic with an inflatable blanket.

Gowns including pneumatic convective devices are also known and provide warmth to patients in a perioperative environment. For example, convective gowns can be used in a preoperative setting, i.e., before surgery and typically while waiting in a different room from the operating room, as comfort warming. Such gowns are not necessarily designed for prewarming, which can be useful in preventing anesthesia-related hypothermia.

SUMMARY

Aspects of the present disclosure can be related to a warming device, systems, and methods of using. The warming device can include a clinical garment comprising a body portion adapted to cover a portion of a patient, an inner surface configured to face the patient, and an outer surface opposite the inner surface. The body portion can include sleeves sized and positioned for receiving the patient's arms. In addition, the clinical garment can include an insulative layer comprising an insulative edge portion disposed on the clinical garment. The insulative edge portion is configured to make the warming device non-linting.

Previous gowns are generally not insulative, particularly with single-use or disposable gowns.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

"Clinical garment" refers to a garment that is typically used to temporarily clothe a person in a clinical setting while awaiting and undergoing treatment. Clinical garments include hospital gowns, robes, bibs, and other equivalents. The clinical setting may be a medical, dental, or veterinary office or clinic, a hospital, or any facility or institution that provides treatment to patients.

"Hemline" refers to the level of the lower edge of a garment.

"Convective" refers to refers to a mode of heat transfer, it being understood that heat may at the same time be transferred between a device according to this invention and a body by conduction and radiation, although not to the degree of convection.

Aspects of the present disclosure relate to a warming device comprising a clinical garment with an insulative layer disposed thereon such that the edge portion of the insulative layer is not exposed. Additional aspects of the present disclosure relate to a pneumatic convective device that is disposed within the warming device.

The pneumatic convective device may be deployed for use with humans, animals, patients, clinicians, practitioners, observers, and so on.

The pneumatic convective device has a pneumatic portion for receiving and distributing at least one stream of pressurized, thermally conditioned air in a structure for being disposed on, adjacent, or next to the core of a body.

The embodiments of the invention illustrated and discussed below are inflatable. That is, their structures, flaccid when not in use, tauten when receiving a stream of pressurized air. The illustrations portray these structures in both inflated and uninflated states, with the understanding that inflation of these embodiments is not necessary to practice of the invention. Indeed, as consideration of the embodiments will make clear, inflatability itself is not necessary to practice of the invention.

In some embodiments, a clinical garment may be specially designed for use with a pneumatic convective device. These specially designed clinical garments would function the same as traditional clinical garments (i.e., temporarily clothe a patient in a clinical setting while awaiting and undergoing treatment) but may include a mounting system for the pneumatic convective device as well as incorporating slits, openings and the like for access to the pneumatic convective device. In other embodiments, the pneumatic convective device is an integral part of the clinical garment.

Figure 1A:
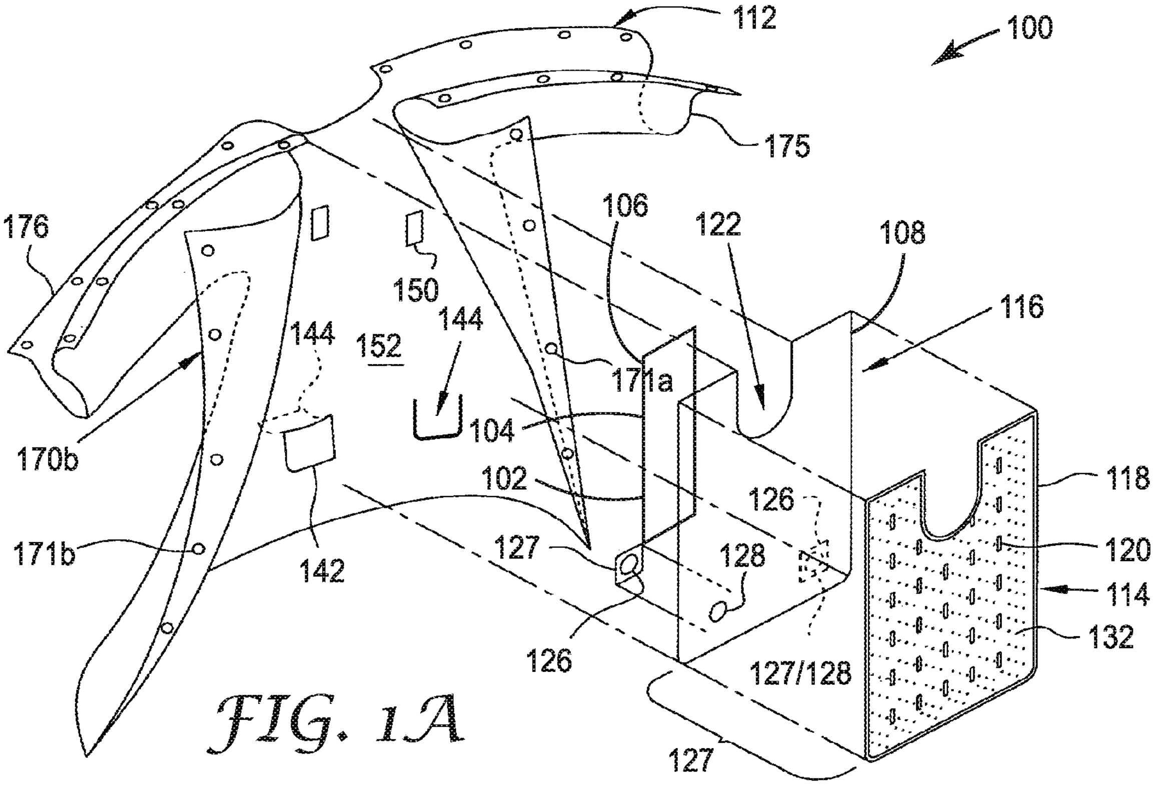
FIG. 1A-1B illustrate a pneumatic convective device that is combined with a clinical garment in accordance with one embodiment.
Figure 1B:
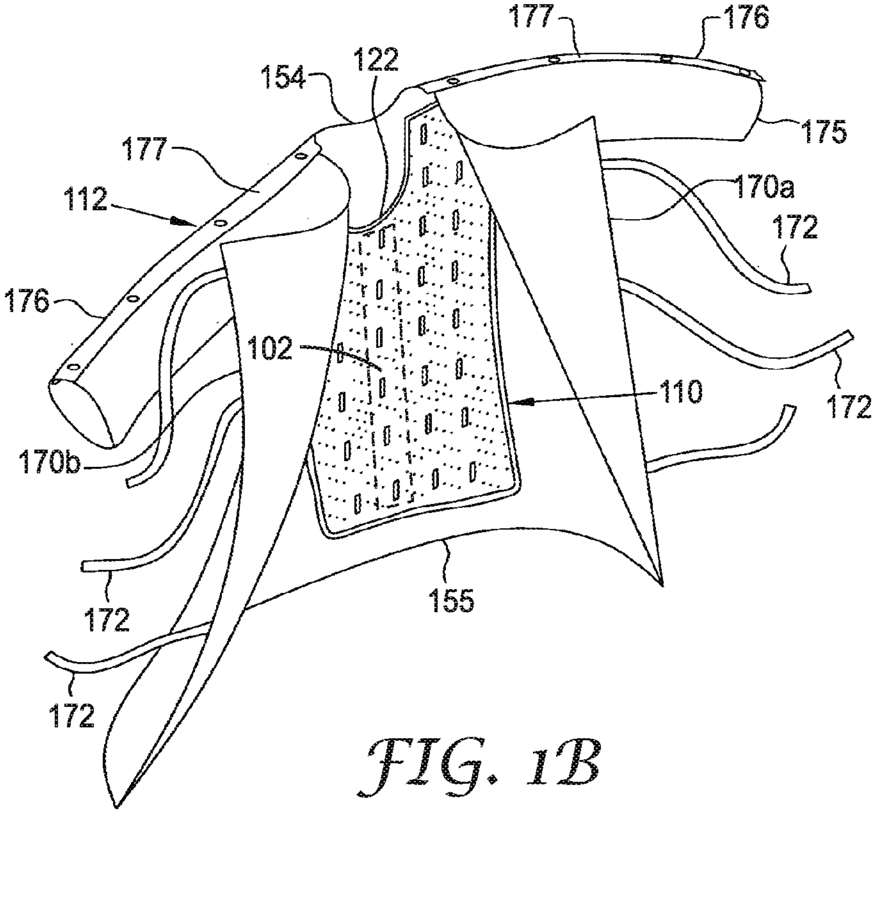

FIGS. 1A-1B illustrate an embodiment of a warming device 100 having an insulative layer 102. The insulative layer 102 can be at least partially covered with a cover element 110 that can be configured to position the insulative layer 102. Although the cover element 110 can be a single layer of air permeable or impermeable material, the cover element 110 can also be a pneumatic convective device 110 with a multi-layer construction. The pneumatic convective device 110 may be attached to or received on a clinical garment 112. In at least one embodiment, the clinical garment 112 is a hospital gown.

In at least one embodiment, the pneumatic convective device 110 includes two generally rectangular sheets 114 and 116 of material that are sealed together continuously at their peripheries 118 and intermittently at multiple locations 120 within their peripheries. As shown, the sheets 114 and 116 have the same generally quadrilateral shape, with an optional U-shaped indentation 122 along one edge. In other embodiments, the pneumatic convective device 110 can be a single sheet of material that is bound to the clinical garment 112 itself as described in FIG. 4.

In at least one embodiment, at least one opening 128 is provided through the sheet 116 (two openings are shown in the figures), and a quadrilateral, hose card 126 with an inlet port 127 is mounted to the sheet 116 over the opening 128, with the inlet port 127 aligned with the hole 128. The at least one opening 128 is provided in communication with the cavity/space between the sheets 114 and 116.

The inlet port 127 may receive the end of an air hose from which a stream of pressurized, thermally-treated air flows, through the opening 128, into the space between the sheets 114 and 116. At least one of the sheets 114 and 116 is permeable to air. In this example, only the sheet 114 is air permeable, although this is not intended to so limit the scope of the invention. The permeability of the sheet 114 may be provided by characteristics of the material from which it is formed; alternatively, holes or apertures 132 may be formed in it during the process which joins the sheets 114 and 116. Or, permeability of the sheet 114 may result from the characteristics of its formative material and from formed apertures.

Thus constructed, the sheets 114 and 116 form between themselves a pneumatic structure to receive and distribute pressurized air within itself. At least one permeable member of the device (the sheet 114, for example) cooperates with the pneumatic structure to emit pressurized air from the device. In this regard, one end of an air hose may be received through an inlet port 127. A stream of pressurized, thermally conditioned air introduced through the air hose will fill the space between the sheets 114 and 116 and be distributed throughout the space. The pressurized air is emitted from the pneumatic structure through the air permeable sheet 114 and the motion of the emitted air supports heat transfer with a body adjacent, next to or near the pneumatic structure, facing the permeable sheet 114.

In at least one embodiment, the clinical garment 112 can be made from a woven cloth, such as cotton, or a non-woven such as spunbond-meltblown-spunbond material (SMS), and the seals between the portion of its inside surface 152 and an optional extruded layer of a laminate sheet may be formed by a gluing, a heating, or an ultrasonic process. Examples of non-woven material include any one or more of polyester, cotton, rayon, polypropylene, and wood pulp. Examples of extruded synthetic material include polypropylene, polyesters, and polyurethanes. In at least one embodiment, the clinical garment can be treated with a material to make a portion of the clinical garment air-impermeable. In at least one embodiment, the clinical garment 112 is a disposable gown that is configured to be single-use by a patient before the clinical garment 112 is disposed as medical waste.

Examples of attachment materials and mechanisms by which the pneumatic convective device 110 as presented in FIG. 1A-B can be attached to the clinical garment 112 include two-sided adhesive, hook and loop, sewing, snaps, heat, ultrasonic, rivets, and any and all equivalents thereof.

As shown in FIG. 1B, the pneumatic convective device 110 is adapted to be mounted to, received on, supported by or otherwise combined with a clinical garment 112. In this embodiment, the clinical garment 112 itself has openings 142 with flaps 144 through which the inlet ports 127 of the device 110 are accessed.

To attach the pneumatic convective device 110 to the clinical garment 112, double-sided adhesive strips 150 may be disposed between the sheet 116 and the inside surface 152 of the clinical garment 112. The adhesion of the sheet 116 with the surface 152 enable the device 110 to be mounted to, received on, supported by or otherwise combined with the clinical garment 112, with the U-shaped indentation 122 adjacent the edge of neck opening 154 of the clinical garment 112 which receives the neck of a user, the sheet 116 facing the inside surface 152, the permeable sheet 114 facing the wearer of the clinical garment 112. In the practice of this invention, the U-shaped indentation 122 is optional, and is not required to practice the invention.

In at least one embodiment, the pneumatic convective device 110 can be releasably attached to the clinical garment 112. For example, the pneumatic convective device 110 can have a strip of releasable adhesive (e.g., 150) that attaches to the clinical garment. In another example, the pneumatic convective device 110 can include a perforation proximate a permanent adhesive such that a user can tear along the perforation cleanly to remove the pneumatic convective device 110. In another example, the pneumatic convective device 110 can include hook and loop.

In at least one embodiment, the pneumatic convective device 110 can be a separate forced air warming blanket such as an upper body blanket that is commercially available as the model 622 under the trade designation Bair Hugger.

The clinical garment 112 has a slit 170 that extends from the neck opening 154 to a hemline 155. In at least one embodiment, the distance from the neck opening 154 to the hemline 155 can be at least 24 inches, at least 30 inches, or at least 36 inches.

To attach the clinical garment 112 to a patient, there is a fastening device provided to provide for ease in securing the clinical garment 112 to the patient as well as allowing for ease in adjusting the size of the clinical garment to accommodate various different size wearers. Fastening devices can be removable or fixed. For example, with removable fastening devices/fasteners, FIG. 1A shows one method using snap buttons 171 *a*, 171 *b* or hook-and-loop positioned along opposing sides of the slit 170 *a*, 170 *b* that can be brought together and fastened to hold the clinical garment to the patient. Another method attachment shown is a plurality of strings 172 positioned along opposing sides of the slit 170 *a*, 170 *b* that can be tied together for hold the clinical garment to the patient. Other removable fastening devices include snaps, repositionable adhesive, hook and loop elements, snaps, and any and all equivalents thereof. Fixed fastening devices can be stronger than the underlying material being bound together. For example, fixed fastening device can include ultrasonic or thermal welding, double-sided adhesive, or rivets.

In some embodiments, the clinical garment may include sleeves that are sized and positioned for receiving a patient's arms. Two examples of suitable sleeves are shown in the figures. In FIGS. 1A-1B, the sleeve portions 175 have slits 176 that run the entire length on the shoulder or top 177. This allows access to the upper body of the patient and allows for opening and closing of the slits 176 in an adjustable fashion using fastening devices. The design shown in FIG. 1A also facilitates the manufacturing of the clinical garment 112 in one piece.

The warming device 100 can have an insulative layer 102 disposed on the clinical garment 112. The insulative layer 102 can be a layer of material with specific thermal (e.g., insulative properties). In at least one embodiment, the insulative layer 102 can be disposed on either the inner surface or the outer surface of the clinical garment 112. As shown in FIGS. 1A-1B, the insulative layer 102 can be disposed between the clinical garment 112 and the pneumatic convective device 110. For example, the insulative layer 102 can be sandwiched between sheet 116 and the clinical garment 112.

In at least one embodiment, the insulative layer 102 can be dimensioned as to not obstruct the opening 144 and/or the inlet port 126. For example, the insulative layer 102 can have cutouts where the openings 144 are located. For example, the insulative layer 102 can be rectangular-shaped and slightly smaller than the pneumatic convective device 110 and also include a U-shaped indentation. For example, a pneumatic device perimeter or area of the pneumatic convective device 110 can be greater than the insulative perimeter 106 (or area defined by insulative perimeter 106) of the insulative layer 102.

In at least one embodiment, the insulative layer 102 can be covered by the pneumatic convective device 110. The pneumatic convective device 110 can also encapsulate the insulative layer 102, particularly the insulative edge portion 104. For example, the pneumatic convective device 110 can be oversized relative to the insulative layer 102.

It has advantageously been found that by treating the insulative edge portion 104, linting can be reduced. For example, insulative edge portion 104 can be the edge face of the insulative layer 102. In at least one embodiment, the insulative edge portion 104 can be sealed or encapsulated in the boundaries of the pneumatic convective device 110, clinical garment 112, or portions thereof. For example, the insulative edge portion 104 is not visible to a clinician or patient. The insulative edge portion 104 can also be sealed using a variety of techniques to prevent the edges from linting. For example, the insulative edge portion 104 can be flame laminated, coated, heated, sintered, sewn, taped, or combinations thereof. In at least one embodiment, the insulative edge portion 104 can refer to a portion of or even the entire perimeter of the insulative layer 102. For example, the insulative edge portion 104 can be taped on one or both sides of the insulative layer 102. A single piece of tape can start on the first surface of the insulative layer 102, cover a side edge of the insulative layer, and end on the second surface of the insulative layer. In at least one embodiment, the treatment can extend at least one-eighth of an inch, at least one-half of an inch, from the insulative edge portion. The treatment can also be no greater than 2 inches from the insulative edge portion. can be treated at least In at least one embodiment, the insulative edge portion 104 can be configured to reduce linting. Linting can refer to the release of material from the insulative layer 102. Linting can be measured using a Gelbo-flex linting test to measure airborne particles shaken from a fabric per cubic foot of air. The standard protocol for linting testing is ASTM 160.1. Particles are typically measured from 0.5 microns or larger in size. As defined herein, non-linting can generally refer to warming devices 100 with treated insulative edge portions 104 having Gelbo-flex particle counts of less than 20,000, less than 10,000, less than 5,000, less than 2,500, less than 1,000, or less than 500.

In at least one embodiment, the standard for testing can be ISO 9073-10 (2003). Under this testing standard, non-linting can also refer to the coefficient of linting for the warming device 100 being no greater than 4.5, or no greater than 4.4, no greater than 4.3, no greater than 4.2, no greater than 4.1, no greater than 4, no greater than 3.9, no greater than 3.8, no greater than 3.7, no greater than 3.6, or no greater than 3.5.

In at least one embodiment, fastening devices such as a fixed fastener can facilitate attaching the insulative layer 102 to the clinical garment 112. In at least one embodiment, pneumatic convective device 110 can be permanently fastened to the clinical garment 112 along the pneumatic device perimeter 108 to form a cavity such that the insulative edge portion 104 is fully encased in the cavity.

The insulative layer 102 can be formed from many appropriate materials or combinations of materials, including, but not limited to, foam, nonwoven and woven materials made from polymers such as polyester, polypropylene, polyethylene, polyethylene terephthalate, polyamides, polyvinyl chloride, acrylics, acrylic copolymers, polystyrene, rayons, acetates, and polysulfone. In a preferred embodiment, insulating layer 12 comprises a microfiber-based web made from polypropylene and polyester as described in U.S. Pat. No. 4,118,531 (Hauser) and commercially available from 3M (St. Paul, Minn.) under the trade designation THINSULATE. Some examples of suitable materials for use as the insulative layer 102 are 20-70 g/m2 THINSULATE, C-type, 60-80 g/m2 THINSULATE, G-type, 65 g/m2 woven nylon, or 182 g/m2 cotton blankets.

In at least one embodiment, the insulative layer 102 can include one or more fabric scrims to contain a nonwoven material. The surface area insulative edge portion 104 can be defined by a thickness of the insulative layer 102. For example, the insulative layer 102 can have a thickness of no greater than 4 cm, no greater than 3 cm, no greater than 2 cm, or no greater than 1 cm as measured using ASTM D 5736 at 0.002 psi. In at least one embodiment, the insulative layer 102 can have a basis weight of between 30 g/m$^2$ to 700 g/m$^2$, and more preferably 40 g/m$^2$ to 100 g/m$^2$ to balance thermal comfort of the patient and prewarming effect.

In at least one embodiment, insulative layer 102 has a thermal resistance value (clo value) of at least 0.3, more preferably 0.5, more preferably 1.0, or even more preferably 1.5. The clo unit is defined as the amount of clothing required by a resting subject to be comfortable at a room temperature of 70° F. (21° C.) using the test method provided in ASTM F 1868, Standard Test Method for Thermal and Evaporative Resistance of Clothing Materials Using a Sweating Hot Plate, Part C (2017). As described herein, the insulative layer 902 can have an R-value of at least 0.5 R, at least 0.6 R, at least 0.75 R, or at least 1 R, or at least 1.5 R.

Optionally, the clinical garment 112 can include an additional barrier layer on the outer surface or the inner surface. The barrier layer can be made of any suitable material that forms an air-impermeable layer. Suitable materials include polyesters (e.g., polyethylene terephthalate, polyethylene naphthalate and polybutylene terephalate and the like), fluorinated layers such as polytetrafluoroethylene (PTFE, e.g., TEFLON), polyamides (e.g., nylon), chlorotriflouroethylene (ACLAR), polyvinylidene fluoride, as well as copolymers of perflourinated monomers with partially fluorinated monomers such as copolymers of tetraflouroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), and polyolefins (e.g., polyethylene, high density polyethylene, polypropylene, and combinations thereof). A metallic foil film laminate barrier layer, such as aluminum foil, metallized paper or metallized polyester, may also be used on the inner surface 152 or outer surface of the clinical garment.

Figure 12:
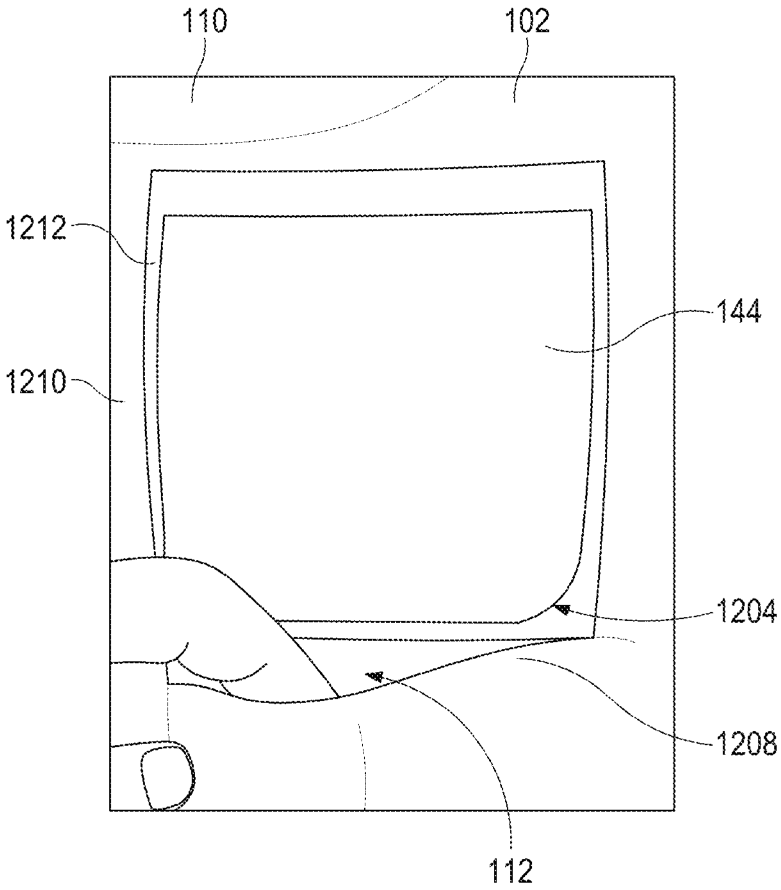
FIG. 12 illustrates an embodiment of the insulative layer on the warming device in accordance with one embodiment.

FIG. 12 illustrates another embodiment of the insulative layer 102. Here, the insulative layer 102 can have a portion removed to form an opening 1204 therefrom to expose the flap 144. The opening 1204 of the insulative layer 102 can have an interior perimeter 1208 that follows the contours of the flap 144. In at least one embodiment, at least a portion of the perimeter 1208 can be secured to the clinical garment 112. For example, adhesive tape 1210 can be disposed along the insulative edge portion 1212 at the interior perimeter 1208 to reduce linting and provide security. Further, the inlet (not shown) of the pneumatic convective device 110 can be accessible via the flap 144 and the opening 1204 of the insulative layer 102.

Figure 2:
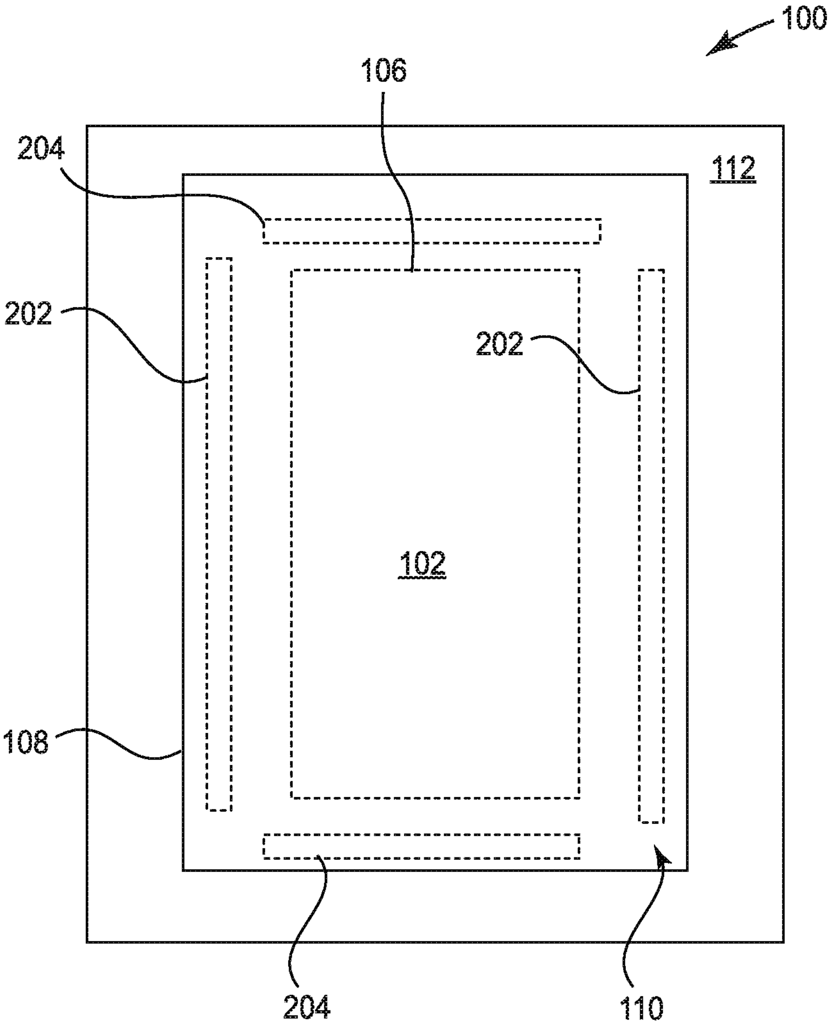
FIG. 2 illustrates a top view of the insulative layer on the warming device in accordance with one embodiment.

FIG. 2 illustrates a top view of the warming device 100 and pneumatic convective device 110 disposed on the clinical garment 112. The clinical garment can include opposed fastening devices 202, and opposed fastening devices 204 proximate the pneumatic device perimeter 108. The fastening devices can (removably or fixedly) attach the pneumatic convective device 110 to the clinical garment 112 and secure the insulative layer 102. In at least one embodiment, the fastening devices can be disposed such that there are gaps between adjacent fastening devices (e.g., between fastening devices 204 and fastening devices 202. In other embodiments, the fastening devices 202 and fastening devices 204 can be connected to each other and continuous along the pneumatic device perimeter 108. In at least one embodiment, the fastening devices can be spaced apart from the pneumatic device perimeter 108 no greater than 2 inches. In at least one embodiment, the fastening devices 202 and fastening devices 204 can be positioned between the insulative perimeter 106 and pneumatic device perimeter 108. In at least one embodiment, the plurality of fastening devices can be distributed throughout the pneumatic convective device 110 and the clinical garment 112. For example, the fastening device can bind the clinical garment, the insulative layer 102 and the pneumatic convective device 110.

In at least one embodiment, the insulative layer 102 can have a surface area that is at least 50 percent, at least 60 percent, at least 70 percent, or at least 80 percent of a surface area of the body portion of the clinical garment 112 (e.g., excluding sleeves). In at least one embodiment, the insulative layer 102 can have a surface area that is at least 15 percent, or at least 30 percent of the surface area of the clinical garment 112 including the sleeves.

In at least one embodiment, the pneumatic convective device 110 can have a surface area that is at least 40 percent, at least 50 percent, or at least 60 percent of the surface area of the clinical garment. In at least one embodiment, the pneumatic convective device 110 can have a surface area greater than the surface area of the insulative layer 102.

Figure 3:
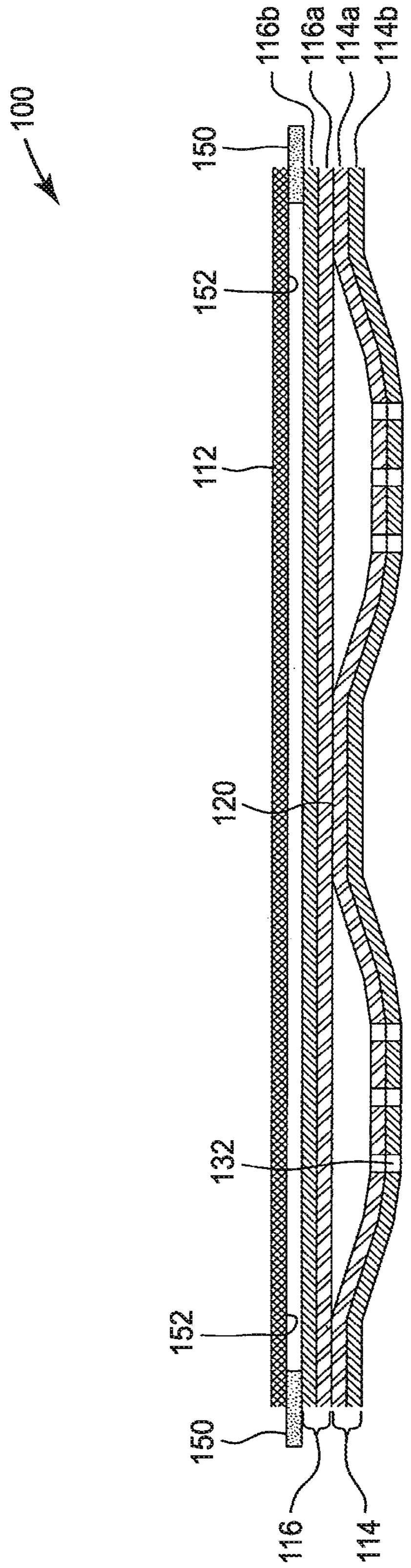
FIG. 3 illustrates a cross-sectional view of the warming device in accordance with one embodiment.

FIG. 3 illustrates a side view of the warming device 100. The sheets 114 and 116 may have an identical laminate structure in which a layer (114*a*, 116*a*) of extruded synthetic material is lined with a layer (114*b*, 116*b*) of non-woven material. If a laminate structure is selected, holes or apertures 132 are formed through both layers 114*a*, 114*b* of the sheet 114. As shown, the sheets 114 and 116 are oriented to have the extruded layers (114*a* and 116*a*) facing, and the seals 118, 120 are formed by a gluing process or by a heating or ultrasonic process acting through one of the layers of non-woven material.

Figure 4:
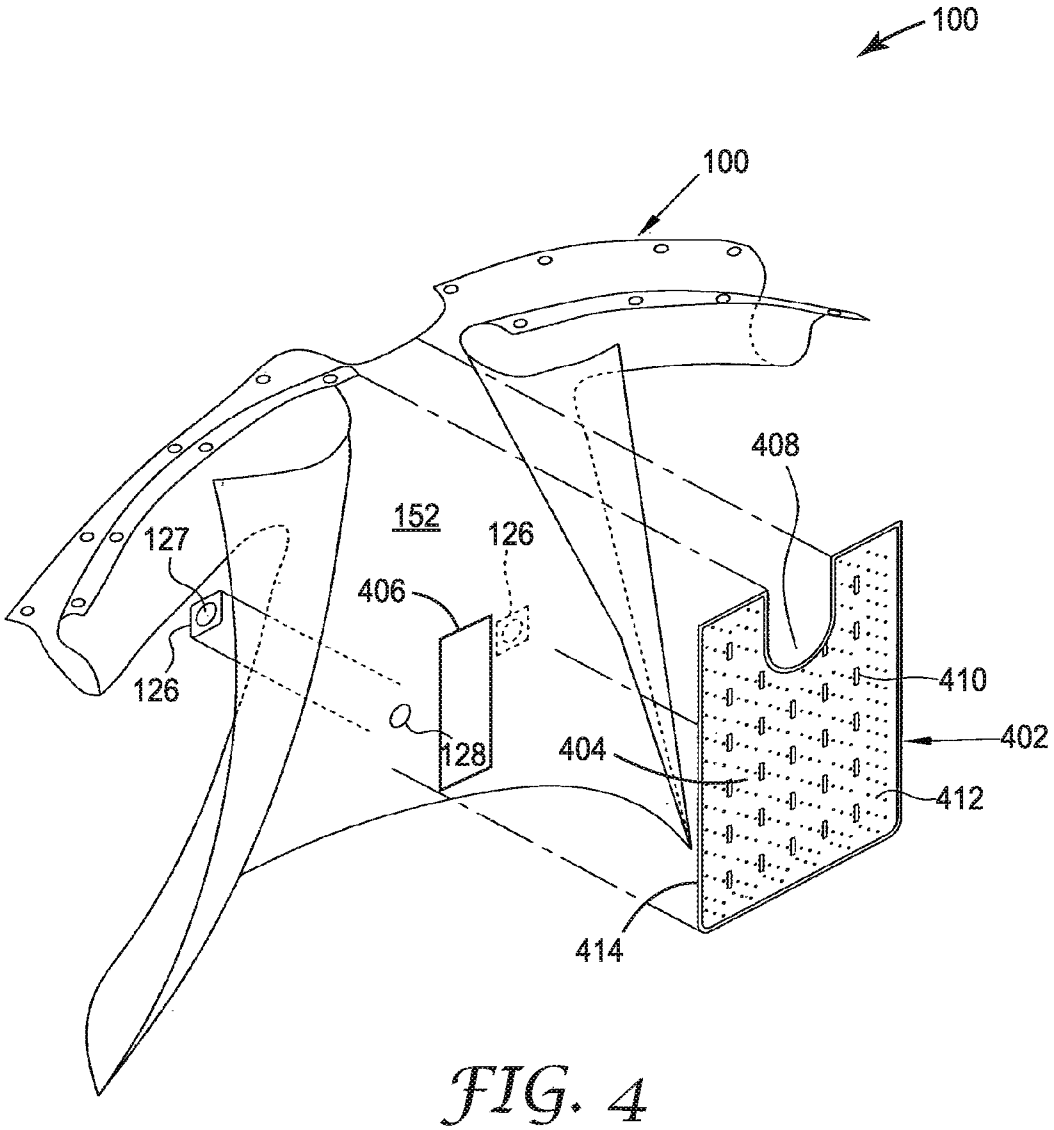
FIG. 4 illustrates a warming device in accordance with one embodiment.

FIG. 4 illustrates an embodiment of warming device 400. In warming device 400, the pneumatic convective device 402 comprises only the sheet 404. In this variant, a portion of the inner surface 152 is incorporated into the structure of the pneumatic convective device 402, serving in the role of the sheet 116 as in FIGS. 1-3. Otherwise, the structure and operation of the pneumatic convective device 402 are as already described. For example, the sheet 404 can be generally rectangular except for u-shaped indentation 408 formed therein. The sheet 404 can have a pneumatic device perimeter 414 and be fixedly attached to the inner surface 152 adjacent to the pneumatic device perimeter 414 forming an air-tight seal. As used herein, adjacent can mean within 2 inches, or within 4 inches. Additional seal 410 and holes or apertures 412 can be present. The seal 410 can be a fixed fastener such as an ultrasonic weld or heat seal between two polymeric layers such as sheet 404 and inner surface 152. The seal 410 can secure portions of sheet 404 to prevent ballooning when the cavity is inflated with warmed air. The seal 410 can penetrate the insulative layer 406 and prevent movement of the insulative layer 406.

In at least one embodiment, the fastening device can be within 2 inches of the pneumatic device perimeter 414 and form an air-tight sealed portion with the inner surface 152. In at least one embodiment, the clinical garment 112 can be made air-impermeable on the portion that is aligned with sheet 404 to prevent air from escaping through the inner surface 152.

In at least one embodiment, the warming device 400 can include an insulative layer 406 which is similar to the insulative layer 102 previously described. The insulative layer 406 can be disposed between sheet 404 and the inner surface 152 and configured to have dimensions similar to insulative layer 102 in FIGS. 1-3. The insulative layer 406 can be contained within the border formed by the sealed portion. Additionally, the seal 410 can prevent movement of the sheet 404. In at least one embodiment, edge portions of the insulative layer 406 can be contained within the seal 410.

In at least one embodiment, the insulative layer 406 can be aligned over the inlet 126 and opening 128 since placement of the insulative layer 406 over the inlet 126 or opening 128 will not interfere with insertion of a hose end.

In at least one embodiment, insulative layer 406 is optional. For example, the sheet 404 can be integrally formed from an insulative layer which has the thermal properties described herein. In this configuration, sheet 404 can be air permeable and/or include holes or apertures 412 and fixedly attached to the inner surface 152. Air from the inlet 126 can flow into the cavity formed between the sheet 404 and the inner surface 152. The warmed air can be diffused to the patient via the sheet 404. This approach can minimize the amount of material and reduce heat loss by a patient.

Although sheet 404 is shown as air-permeable, the device shown in FIG. 4 may be constructed with an impermeable sheet on the outside of the clinical garment 112, wherein the portion of the clinical garment 112 that includes the inner gown surface 152 would serve as the permeable sheet.

Figure 5:
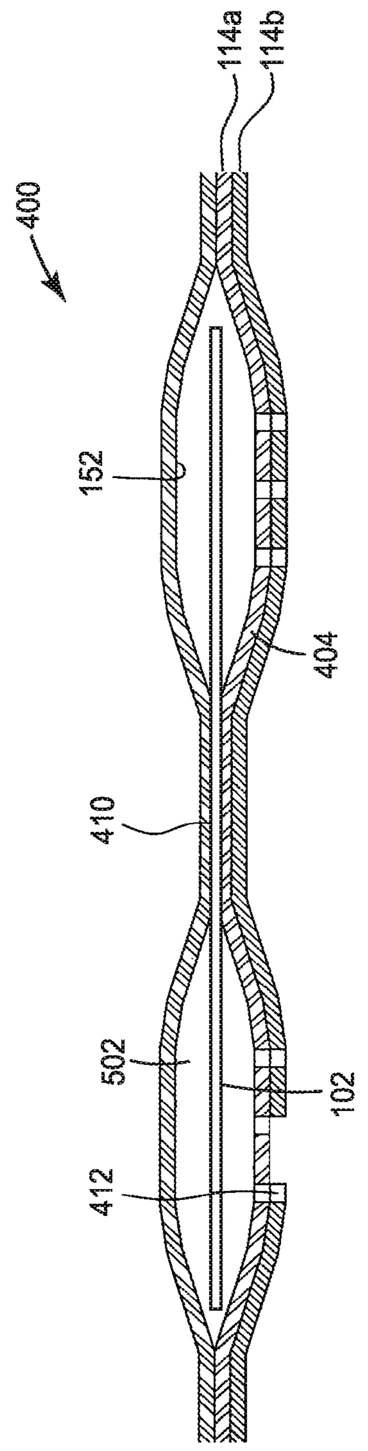
FIG. 5 illustrates cross-sectional view of the warming device in accordance with one embodiment.

In FIG. 5, a cross-sectional view of a portion of the pneumatic convective device 402 is shown. As described, sheet 404 may be a laminate structure as described in FIG. 3. As shown, the seal 410 can penetrate the insulative layer 102 if present. When inflated, a cavity 502 formed between inner surface 152 and the sheet 404 can fill with warmed air. The warmed air can then exit the holes or apertures 412 of the pneumatic convective device 402 which can then be provided to a patient. In at least one embodiment, apertures 412 can refer to openings within a sheet (e.g., 404*a*) with the openings being less than 3 $mm^2$.

Figure 6B:
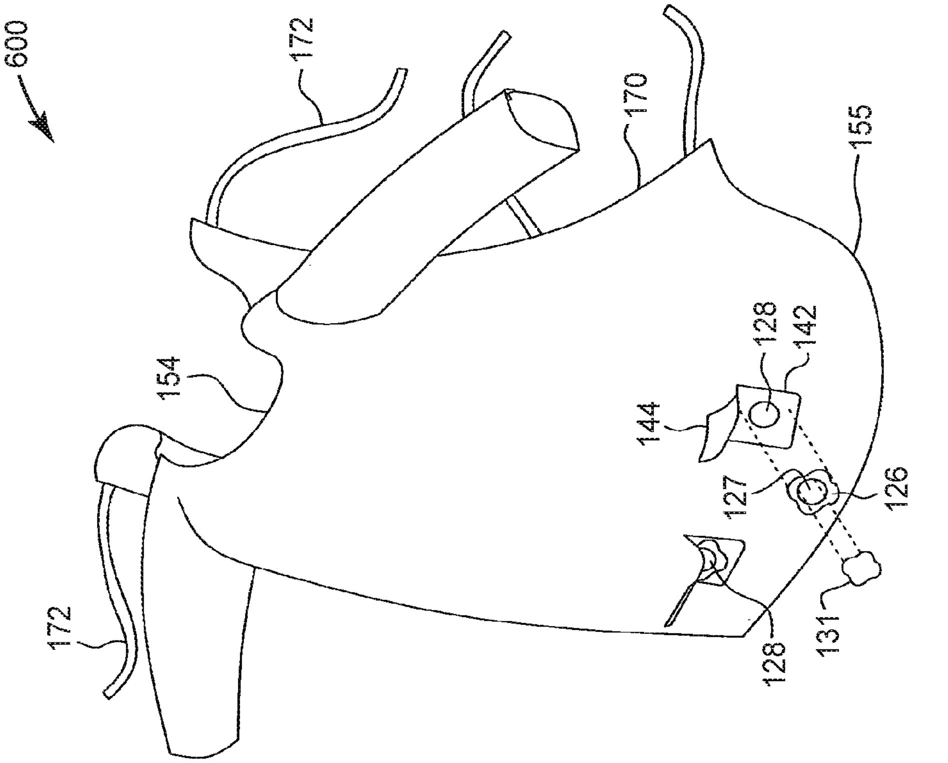
FIG. 6A-6B illustrate a warming device 600 in accordance with one embodiment.
Figure 6A:
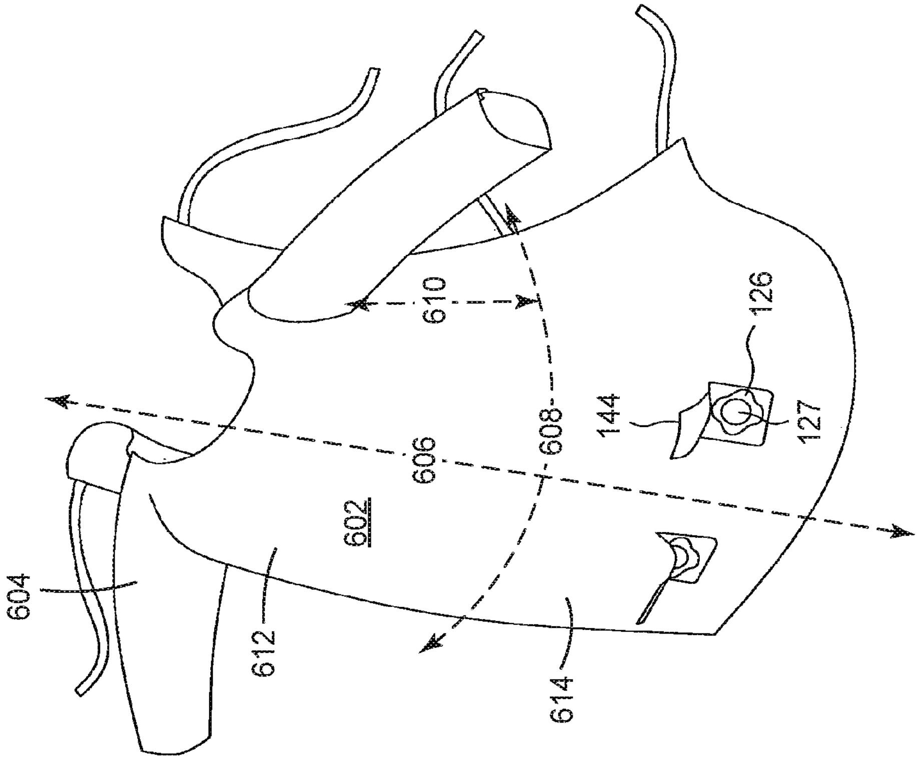

FIGS. 6A-6B show the front of the clinical garment 112 which can refer to either the embodiment in FIGS. 1-3 or the embodiment in FIGS. 4-5. The inlet ports 127 are accessible from the front of the clinical garment 112. There may be one or more inlet ports 127 providing access through openings 128. In these cases, it may be desirable to plug an inlet port 127. An inlet port plug 131 may be used to close the inlet ports 127 that are not in use with the air hose. Many types of plug may be used to close the inlet ports 127, such as those described in U.S. Pat. No. 5,997,572.

In at least one embodiment, the clinical garment 112 is oriented longitudinally along the longitudinal axis 604. The clinical garment 112 can be divided into a body portion 602 and a sleeve portion 604. The sleeve portion 604 can be established by the boundaries of the sleeves. The body portion 602 can be configured to cover the torso and a portion of the legs of a patient. In at least one embodiment, the body portion 602 can further be divided into one or more regions. For example, the body portion 602 can be intersected by line 608 which can divide the body portion 602 into the torso portion 612 and the leg portion 614. The line 608 can align with the transverse plane, or axial plane of a patient. For example, the torso portion 612 can correspond to the superior part of the patient and the leg portion 614 can correspond to the inferior part of the patient.

In at least one embodiment, a distance 610 from the base of an armhole of the sleeve portion 604 (corresponding to an arm pit of a patient) to line 608 can be no greater than 20 inches, no greater than 18 inches, or no greater than 16 inches.

Figure 7:
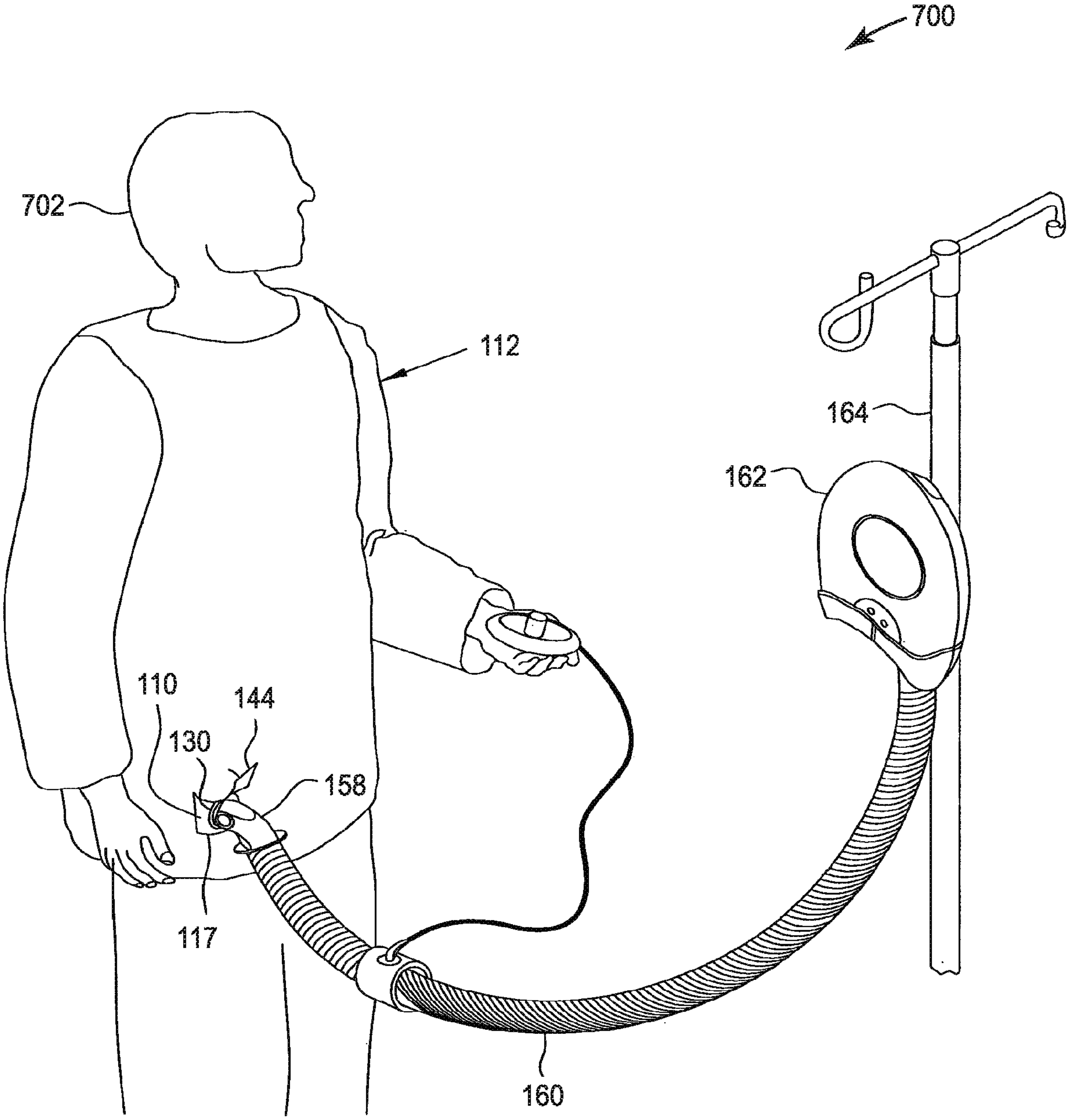
FIG. 7 is a perspective view drawing showing engagement of the combination in a warming system in accordance with one embodiment.

FIG. 7 illustrates a warming system 700 comprising a patient 702 (shown in the standing position) wearing the clinical garment 112 which includes the embodiment using the pneumatic convective device 110 or pneumatic convective device 402, as described above. The patient 702 may be in a doctor's office in an out-patient facility, or any other suitable location. The clinical garment 112 is shown with connecting lines that illustrate how it would be attached to the patient 702. An end 158 of an air hose 160 is connected to the pneumatic convective device 110 may be received with the hose card 130 to provide a stream of pressurized, thermally treated air directed into the device 110 through inlet port 127.

For the embodiment shown in FIGS. 1-3, the flap 144 is lifted, exposing the inlet port 127 and the hose card 130, through gown opening 142. For the embodiment shown in FIGS. 4-5, access to the hose card 130 is on the front of the clinical garment 112 (there is no gown opening). The other end of the air hose 160 is connected to a warming unit 162 that can provide a stream of pressurized, thermally controlled air to the device. Warming units and components can be commercially available as model 675, model 775 or model 875 under the trade designation Bair Hugger.

The temperature at the hose-end 158, prior to the air entering the pneumatic convective device 110, may range from ambient to up to 46° C. The average air temperature delivered to the patient 702 may be less than this, depending on the gown design. The airflow at the hose-end 158, prior to the air entering the pneumatic convective device 110, may be between 5-15 CFM or even 30-50 CFM. In at least one embodiment, the airflow can be at least 20 CFM, at least 30 CFM, or at least 40 CFM. The pressure inside the pneumatic convective device 110 may range of 0.05 to 1.2 inches $H_2O$. The warming unit 162 may be mounted on an IV pole 164, as illustrated.

When the stream of pressurized, thermally treated air is provided to the pneumatic convective device 110, the pneumatic convective device 110 tautens and air is emitted through the sheet 114, treating the patient 702 with thermally controlled air. As can be appreciated with reference to FIG. 7, with the clinical garment 112 worn by a patient 702, the pneumatic convective device 110 is disposed so that the permeable sheet 114 faces the patient 702 primarily in the region between the person's neck and thighs. Thus, when pressurized, thermally treated air is provided to the pneumatic convective device 110, it is distributed within the device, and emitted through the sheet 114, focusing or concentrating the emitted air primarily on the patient 702's upper thorax. Convection will then cause heat transfer between the emitted, thermally treated air and the person's body core or diminish heat loss from the person's body to the environment.

The clinical garment described in the above and in below-described embodiments may be a standard gown, a modified gown or a special purpose gown. The gowns may have rear openings, front openings or other openings suitable openings, such as a head opening in a poncho type gown. One type of gown shown in the figures has a rear opening.

Figure 8:
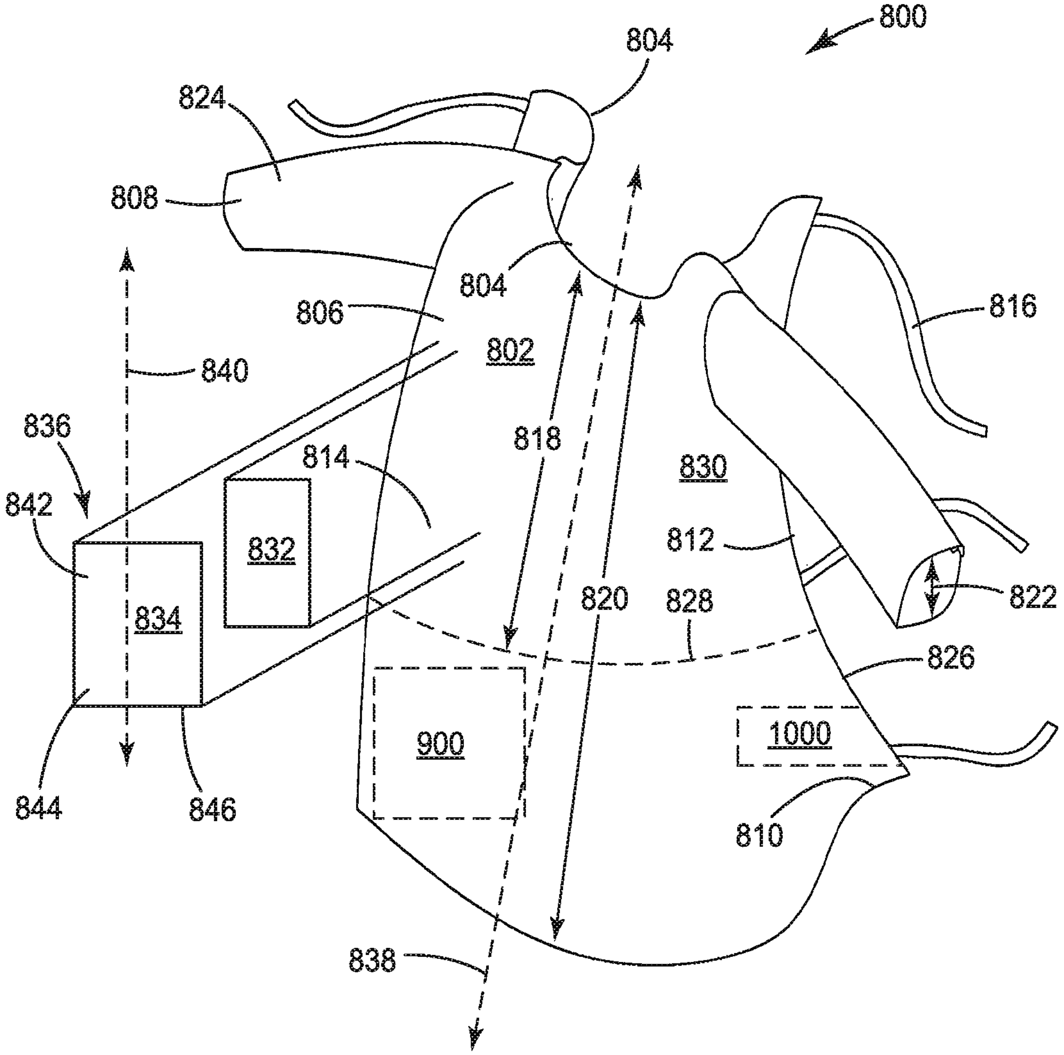
FIG. 8 illustrates a warming device 800 in accordance with one embodiment.

FIG. 8 illustrates a warming device 800. The warming device 800 comprises a clinical garment 802 having an insulative layer disposed on at least a portion thereon or formed therefrom. The warming device 800 can differ from the warming device 100 and the warming device 400 in that the warming device 800 can but does not necessarily include a pneumatic convective device. An insulative clinical garment 802 can be particularly advantageous in situations where a pneumatic convective device and the associated warming unit may not be practical. In at least one embodiment, the insulative layer can have a surface area that is at least 50%, at least 60%, at least 70%, at least 80%, at least 90% of the total surface area (e.g., inner or outer surface, body and sleeves) of the clinical garment 802.

In at least one embodiment, the clinical garment 802 can be structured similarly to the clinical garment 112 as described herein except without the openings. The clinical garment 802 can have body portion 830 and sleeves 808. The body portion 830 can have outer surface 824.

The clinical garment 802 can have a neck opening 804 and a hemline 810. The clinical garment 802 can have at least one opening into the clinical garment 802. For example, a slit 812 (preferably rear) through the clinical garment 802 can create an opening for a patient to easily remove the clinical garment 802. Fastening devices 816 can releasably fasten opposing ends of the slit together such that the clinical garment 802 does not fall off of the patient.

In at least one embodiment, the body portion 830 can be separated into a torso portion 814 that aligns with a patient's torso. The torso portion 814 can be established by the line 828 which can align with the traverse plane of the patient. The dimension 818 from the neck opening 804 to the line 828 can be no greater than 32 inches, no greater than 30 inches, or no greater than 28 inches. The dimension 820 from the neck opening 804 to the hemline 810 (along a longitudinal axis 838 from a nadir of the neck opening) can be from 30 inches to 56 inches. Preferably, the dimension 820 can be from 40 to 46 inches.

The sleeves can have a dimension 822 (e.g., a diameter). In at least one embodiment, the dimension 822 can vary from the armhole end near the torso portion 814 vs the cuff end near the hands of a patient. In at least one embodiment, the dimension 822 can be between 6 to 15 inches, 8 to 15 inches, 10 to 15 inches, or 10 to 14 inches near the cuff end.

In at least one embodiment, the clinical garment 802 can include a pocket 836 dimensioned to receive a pneumatic convective device 832. The pneumatic convective device 832 can be an upper body blanket commercially available as the Bair Hugger model 622 from 3M. In at least one embodiment, the pneumatic convective device 832 is folded and is preferably sealed in a sealed package.

In at least one embodiment, the pocket 836 can be formed from a pocket sheet 834 and the outer surface 824. The pocket sheet 834 is formed from a sheet of material that is the same as the clinical garment 802. Pocket sheet 834 can be attached to the clinical garment 802 anywhere on the body portion 830 but preferably on the torso portion 814, and most preferably on the front portion (defined by the chest of the patient) and on the outer surface 824. In at least one embodiment, the pocket sheet 834 can be within 10 inches of any portion of the neck opening 804. In at least one embodiment, the pocket 836 can be disposed on the inner surface of the clinical garment 802. For example, the pocket sheet 834 can be disposed on the inner surface.

The pocket sheet 834 can be attached via an adhesive or stitching along any portion of the pocket sheet perimeter 846, including along the entire pocket sheet perimeter 846. In at least one embodiment, the pocket sheet 834 is attached to the clinical garment 802 at the sides and the pocket end 844.

The pocket sheet 834 can have a pocket end 842 and pocket end 844 that are opposing and oriented along the pocket axis 840. In at least one embodiment, the angle formed between the pocket axis 840 and longitudinal axis 838 is less than 90 degrees (i.e., no greater than perpendicular).

The distance from pocket end 842 to pocket end 844 can be larger than that of the width of the pocket sheet 834. In at least one embodiment, the pocket sheet 834 can have a line of weakness such as a perforation that is configured to break upon a force applied. For example, the pocket sheet 834 can surround the pneumatic convective device 832 on the outer surface 824 of the clinical garment 802. A user can break the line of weakness of the pocket sheet 834 to extract the pneumatic convective device 832 from pocket 836.

Figure 9:
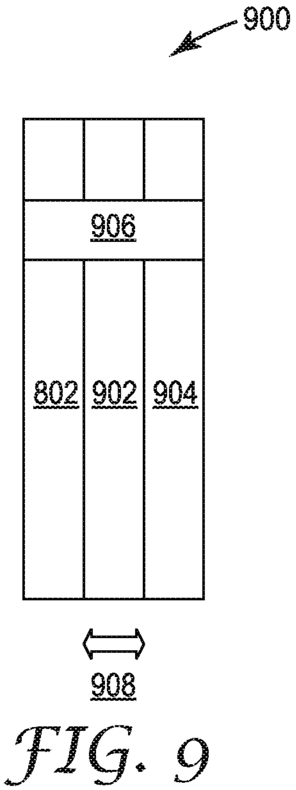
FIG. 9 illustrates a region 900 in accordance with one embodiment.

FIG. 9 illustrates a side cross-sectional view of the region 900 of warming device 800. The clinical garment 802 can be formed from a material that is typically used to make disposable or non-disposable gowns and described herein.

The clinical garment 802 includes at least one portion having an insulative layer 902 disposed thereon. The insulative layer 902 can have a thickness 908. In at least one embodiment, the thickness 908 is no greater than 5 cm. Preferably, the thickness 908 is no greater than 1.5 cm. The insulative layer 902 can have properties similar to embodiments described herein.

The cover element 904 can a woven or non-woven fabric configured to contain the insulative layer 902. The cover element 904 is preferably water-resistant and can resist absorption of bodily fluids. In at least one embodiment, cover element 904 can also be a polymeric film such as a polyester film (e.g., including polyethylene terpthalate), with or without a metalized layer. The cover element 904 can be configured to cover the insulative layer 902 such that the insulative edge portion (partially defined by the thickness 908) is not exposed. In at least one embodiment, the cover element 904 can be a scrim which can be a woven or nonwoven fabric configured to contain or strengthen a combo web of the insulative layer 902). The cover element 904 can be one or more layers of a pneumatic convective device or can refer generally to the pneumatic convective device itself.

The cover element 904 can be attached to the clinical garment 802 via fastening device 906. The fastening device 906 can either penetrate insulative layer 902 or avoid disrupting the integrity of the insulative layer 902. The fastening device 906 is preferably a fixed fastener and can include welded seals or adhesive but could also include mechanical fasteners such as rivets, or stitching. In at least one embodiment, if the fastening device 906 avoids penetrating the insulative layer 902, then the fastening device 906 can directly attach the cover element 904 to the clinical garment 802 and sandwich the insulative layer 902.

Although pictured as showing the insulative layer 902 on the inner surface of the clinical garment 802, the insulative layer 902 and cover element 904 can also be disposed on the outer surface of clinical garment 802.

Figure 10:
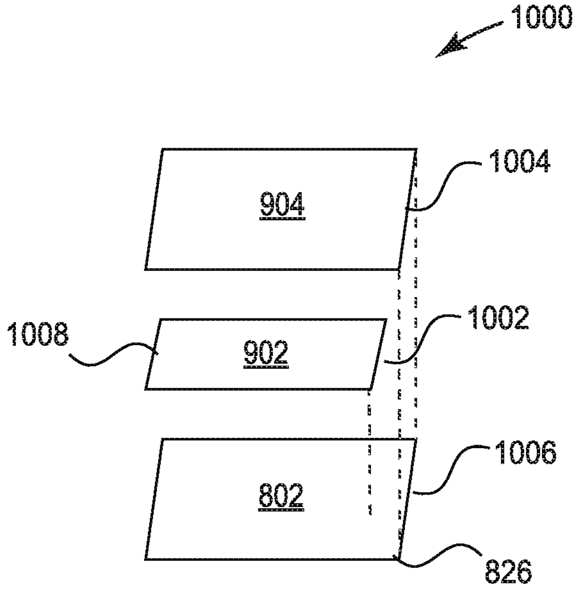
FIG. 10 illustrates a region 1000 in accordance with one embodiment.

FIG. 10 illustrates a perspective view of the different layers of region 1000 of warming device 800. The region 1000 can be similar in construction to FIG. 9. In at least one embodiment, the insulative layer 902 can have an insulative perimeter 1008 for each insulative layer component. The insulative perimeter 1008 can be less than the outer perimeter 826 of the clinical garment 802.

The cover element 904 can be sealed to the clinical garment 802 via a heat or ultrasonic seal forming sealed portion 1004 and sealed portion 1006. As shown, the insulative edge portion 1002 does not extend past the sealed portion 1004 or sealed portion 1006. In at least one embodiment, insulative edge portion 1002 can extend past the sealed portion 1004 and be treated such that linting is reduced.

Figure 11:
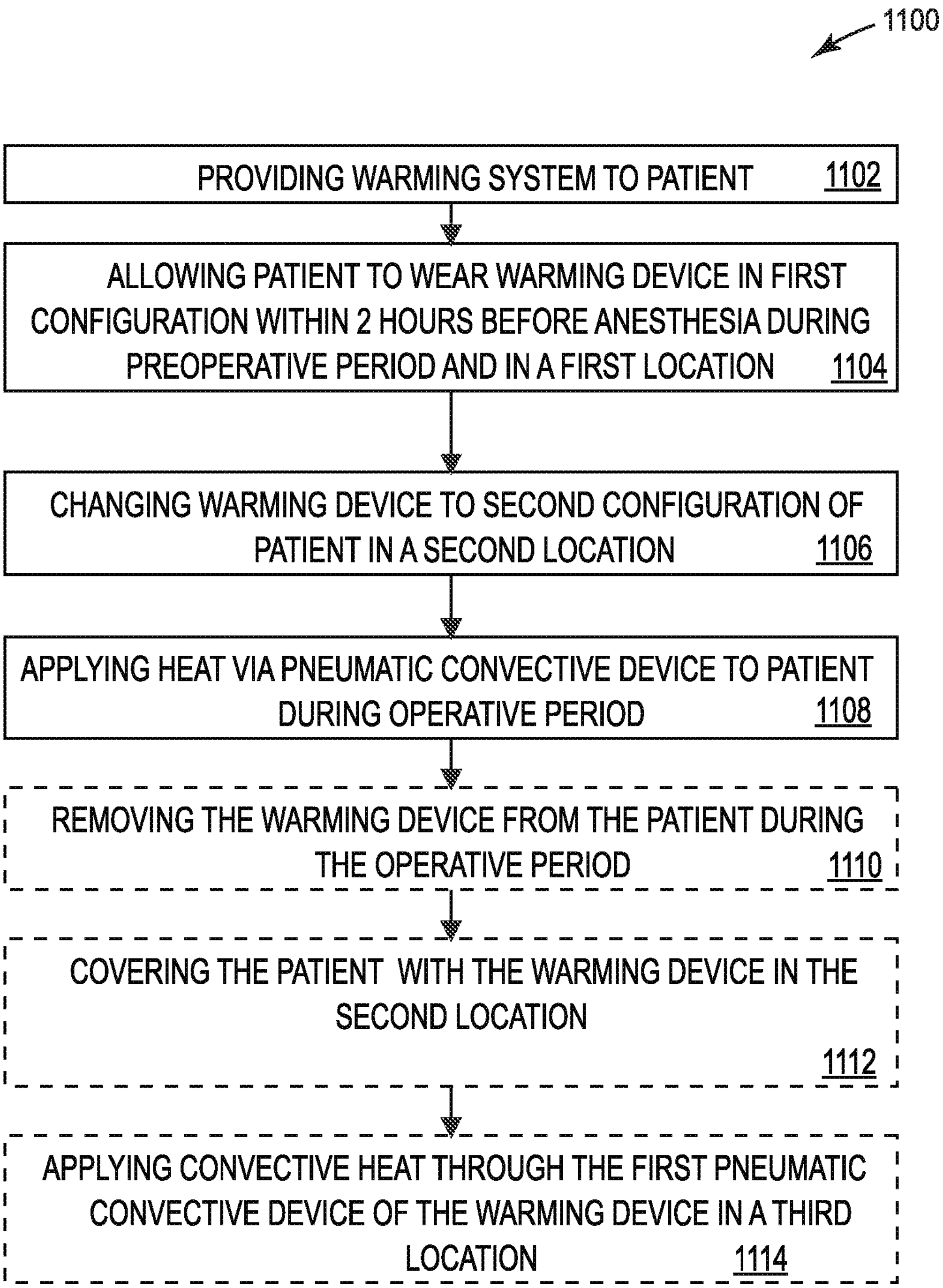
FIG. 11 illustrates a routine in accordance with one embodiment.

FIG. 11 illustrates a flowchart of a method 1100 of applying therapeutic warming to a patient.

The method 1100 can begin at block 1102. In block 1102, the warming system described herein can be provided to the patient. A manufacturer can provide one or more of the components of the warming system to the clinician who can further provide it to the patient according to the instructions of the manufacturer. In block 1104, the clinician can allow the patient to wear the warming device that can include at least a first pneumatic convective device. The patient can wear the warming device during a preoperative period of a perioperative period. For example, the patient can preferably wear the warming device within 2 hours, within 1 hour, or within 30 minutes before anesthesia.

The warming device can help to pre-warm the patient before the anesthesia sufficient to maintain normothermia during anesthesia. Optionally, block 1104 can also include applying heat to the patient via a first pneumatic convective device that is fixedly attached to the warming device. The clinician can activate an active convective heat modality for the warming device. The heat application during block 1104 can result in pre-warming prior to anesthesia. In at least one embodiment, the warming device can contain a passive modality for pre-warming the patient and reducing heat losses. For example, the warming device can also have an insulative material that can reduce heat loss by the patient.

In at least one embodiment, the clinician can place the warming device onto the patient in a first location. For example, the first location can be dependent on hospital configurations, but the first location can be a separate surgical waiting area, a patient recovery room, or preoperative bay. Preferably, the first location can have a power outlet.

In block 1106, the clinician can change the warming device from a first configuration to a second configuration before anesthesia in a second location. In at least one embodiment, the second location is an operating theatre, or operating room where the surgery is taking place. In at least one embodiment, the first location and the second location are the same. For example, pre-warming of the second configuration can be related to a feature of the warming device. For example, the second configuration can be an opened pocket, a removable pneumatic convective device, or a deployment of a pneumatic convective device.

For example, in the current configuration, the first configuration can be in the worn configuration as a patient wears the clinical garment. This may include fastening the fastening devices of the clinical garment. In the second configuration, the clinician can remove a pneumatic convective device that is releasably attached to the surface of the clinical garment or an integrated pneumatic convective device thereon. The pneumatic convective device can be fastened with a repositionable adhesive, which is effective to allow the repositioning of the adhesive article from the first application surface to the second application surface without leaving any visible residue of the pressure sensitive adhesive on the first application surface, the visible residue being any residue that is visible to the unaided eye of a human being.

The changing to the second configuration can also occur during the operative period of the perioperative period. In at least one embodiment, the operative period can begin within 10 minutes, or within 5 minutes before anesthesia is delivered and continue while the patient is anesthetized. In at least one embodiment, the changing of the warming device configurations can occur at least 5 minutes before, at least 10 minutes before the start of anesthesia. In another embodiment, the changing can occur during anesthesia of the patient.

In block 1108, the clinician can apply heat to the patient during the operative period. The total amount of heat is dependent on the clinician preferences; however, the convective warming unit can be capable to output at least 300 watts, at least 350 watts, or at least 400 watts at a hose end.

In at least one embodiment, the power consumption of the convective warming unit can be at least 1400 watts. The heat applied can be sufficient to maintain normothermia of a patient. In at least one embodiment, the heat can be applied through the warming device or from a separate pneumatic convective device that is attached thereon.

Block 1110 to block 1114 can be optional. In block 1110, the clinician can remove the warming device from the patient during the operative period. For example, during a surgical procedure, the warming device can interfere with some surgical procedures (such as an abdominal incision). Thus, to provide warming, the warming device can be removed to expose a surgical treatment area, and optionally apply the heat via a separate pneumatic convective device that is part of the warming system. The warming device can be set aside for later use.

In block 1112, the clinician can retrieve the warming device and cover the patient with the warming device. For example, after the surgical procedure is over, but while the patient is anesthetized, the clinician can cover the patient for modesty in the second location. After the patient is covered, then the patient can be transported to a third location. The third location can be a post-operative recovery bay (i.e., PACU) or a patient room. In at least one embodiment, the separate pneumatic convective device can be discarded.

In block 1114, the clinician can apply heat to the patient through the first pneumatic convective device attached to the warming device. The heat can be such that the patient is comfort warmed during the post-operative period of the perioperative period. The post-operative period can generally be in the third location. In at least one embodiment, the heat can be for comfort warming during block 1114. For example, the heat can be no greater than 500 watts, no greater than 400 watts, or no greater than 200 watts.

List of Illustrative Embodiments

1. A warming device, comprising:
   a clinical garment comprising a body portion adapted to cover a portion of a patient, an inner surface configured to face the patient, and an outer surface opposite the inner surface, wherein the body portion includes sleeves sized and positioned for receiving the patient's arms;
   an insulative layer disposed on the clinical garment, wherein the insulative layer is configured to make the warming device non-linting.
2. The warming device of embodiment 1, wherein the insulative edge portion is covered by a cover element attached to a portion of the outer surface.
3. The warming device of any of the preceding embodiments, wherein the insulative edge portion is covered by a cover element attached to a portion of the inner surface.
4. The warming device of any of the preceding embodiments, wherein the insulative layer comprises a nonwoven having a basis weight of between 20 g/m2 and 210 g/m2, and a thickness between 0.1 cm and 2.1 cm.
5. The warming device of embodiment 4, wherein the insulative layer comprises a scrim sandwiching the nonwoven.
6. The warming device of embodiment 2, wherein the insulative layer has an insulative perimeter and is sandwiched between the cover element and the clinical garment.
7. The warming device of embodiment 6, wherein the cover element and the clinical garment are sealed together proximate an outer perimeter to form a sealed portion, wherein the insulative edge portion does not contact the sealed portion.

7a. The warming device of embodiment 7, wherein the insulative edge portion is attached to the clinical garment via tape along at least part of the insulative perimeter.

8. The warming device of any of the preceding embodiments, further comprising:
   a first pneumatic convective device disposed adjacent to the inner surface;
   an opening formed in the clinical garment for admitting a stream of pressurized, warmed air into the pneumatic convective device.

9. The warming device of any of the preceding embodiments, wherein the insulative layer has an R-value of between 0.5 and 3 R, inclusive.

10. The warming device of any of the preceding embodiments, wherein the insulative layer is disposed on at least a portion of the body portion.

11. The warming device of embodiment 10, wherein the insulative layer is disposed on at least a portion of the sleeves.

12. The warming device of any of the preceding embodiments, wherein the clinical garment has a first side and a second side, the first side has a first garment surface area, that includes the body portion and the sleeves, the insulative layer has a second surface area, the second surface area is at least 15% of the first garment surface area.

13. The warming device of any of the preceding embodiments, wherein the insulative layer is disposed on the outer surface of the clinical garment.

14. The warming device of any of the preceding embodiments, wherein the insulative layer is disposed on the inner surface of the clinical garment.

15. The warming device of any of the preceding embodiments, wherein the body portion further includes a neck opening and a hemline, a rear slit extending from the neck opening to the hemline and fastening devices near the rear slit for detachably attaching opposing sides of the rear slit.

16. The warming device of any of the preceding embodiments, wherein one of the sleeves has a slit, and a fastening device configured to detachably attach opposing sides of the slit.

17. The warming device of embodiment 16, wherein the fastening device selected from the group consisting of buttons, string, snaps, repositionable adhesive, hook and eye elements, double-sided adhesive, hook and loop elements, and rivets.

18. The warming device of any of the preceding embodiments, wherein the clinical garment comprises a nonwoven material.

19. The warming device of any of the preceding embodiments, wherein the clinical garment is integrally formed from an insulative layer.

20. The warming device of any of the preceding embodiments, wherein the clinical garment comprises an opening comprising a liftable flap.

21. The warming device of any of the preceding embodiments, wherein the opening comprises a hose card attached to the outer surface with an inlet port mounted to the first pneumatic convective device.

22a. The warming device of any of the preceding embodiments, wherein the hose card is accessible through the liftable flap.

22b. The warming device of any of the preceding embodiments, wherein the insulative layer has an opening formed therein, the opening has an interior perimeter, wherein at least a portion of the interior perimeter includes the insulative edge portion.

22. The warming device of any of the preceding embodiments, wherein the insulative layer is a synthetic fiber thermal insulation.

23. The warming device of embodiment 22, wherein the synthetic fiber thermal insulation comprises fibers that are less than 20 microns in average diameter.

24. The warming device of embodiment 23, wherein the synthetic fiber thermal insulation comprises polyolefin fibers, polyester fiber, or polyimide fibers.

25. The warming device of embodiment 24, wherein the polyolefin fibers comprise polyethylene terephthalate, polypropylene, or combinations thereof.

26. The warming device of any of the preceding embodiments, wherein the first pneumatic convective device comprises:
   a first layer comprising an air permeable sheet of material having a pneumatic device perimeter.

27. The warming device of embodiment 26, wherein a cavity is formed between the first layer and the inner surface of the clinical garment, wherein the first layer has a patient facing surface and a cavity facing surface.

28. The warming device of embodiment 27, wherein the first layer forms an inflatable perimeter seal at or adjacent to the pneumatic device perimeter with less than all of the inner surface of the clinical garment to form the first pneumatic convective device.

29. The warming device of embodiment 28, wherein the insulative layer is disposed between the cavity facing surface and the inner surface.

30. The warming device of embodiment 29, wherein the insulative layer has an insulative perimeter, the insulative perimeter does not extend beyond the inflatable perimeter seal.

31. The warming device of embodiment 30, wherein the insulative perimeter does not bond with the inflatable perimeter seal.

32. The warming device of embodiment 30, wherein the clinical garment is air-impermeable in a portion aligned with the first layer.

33. The warming device of embodiment 26, the first pneumatic convective device further comprising:
   a second layer having a cavity-facing surface and an outer surface, joining the first layer by an inflatable perimeter seal around the pneumatic device perimeter to form a pneumatic structure, wherein the second layer is air-impermeable.

34. The warming device of embodiment 33, wherein the insulative layer is attached to the outer surface of the second layer.

35. The warming device of embodiment 33, wherein the insulative layer is disposed between the second layer and the inner surface.

36. The warming device of embodiment 35, wherein the insulative layer is attached to the inner surface of the clinical garment.

37. The warming device of any of the preceding embodiments, wherein the clinical garment has a longitudinal axis oriented longitudinally.

38. The warming device of embodiment 37, further comprising a pocket having a first pocket end and a second pocket end oriented along a pocket axis, wherein an angle formed between the pocket axis and the longitudinal axis is less than 90 degrees.

39. The warming device of embodiment 37, wherein the clinical garment comprises a pocket sheet having sides and a first pocket end, wherein the pocket sheet is attached to the clinical garment at the sides and the first pocket end, and unattached or releasably attached to the clinical garment at the second pocket end to form the pocket.

40. The warming device of embodiment 37, wherein a portion of the pocket intersects the longitudinal axis.

41. The warming device of embodiment 37, wherein the pocket is located within 10 inches of a portion of a neck opening.

42. The warming device of embodiment 37, wherein the pocket is dimensioned to receive an second pneumatic convective device in a sealed package.

43. The warming device of embodiment 42, wherein the sealed package has a volume of no greater than 40 cubic inches when the second pneumatic convective device is folded.

44. The warming device of embodiment 42, wherein a portion of the sealed package is releasably attached to the clinical garment along the longitudinal axis.

45. The warming device of any of the preceding embodiments, wherein the sleeve length is no greater than 40 inches.

46. The warming device of any of the preceding embodiments, wherein a sleeve width is at least 9 inches at an armhole of the clinical garment.

47. The warming device of embodiment 46, wherein the sleeve width is at least 5 inches at a cuff.

48. A system comprising the warming device of any of embodiment 1 to embodiment 37.

49. The system of any of the preceding embodiments, further comprising:

a warming unit;

a hose end configured to mate with the inlet of the pneumatic convective device.

50. The system of any of the preceding embodiments, further comprising: a second pneumatic convective device.

51. The system of any of the preceding embodiments, wherein the second pneumatic convective device is wrapped in a sealed package.

52. The system of any of the preceding embodiments, further comprising a patient.

53. A method comprising:

providing the warming system of embodiments 1 to 52 to a patient;

allowing the patient to wear the warming device in a first configuration within 2 hours before anesthesia during a preoperative period and in a first location;

changing the warming device to a second configuration at least 10 minutes before, at least 5 minutes before the start of anesthesia, or during anesthesia of a patient at a second location;

applying heat via a pneumatic convective device to the patient during an operative period.

54. The method of embodiment 53, wherein the first configuration of the warming device comprises a first pneumatic convective device fixedly attached to the clinical garment and a pocket with the second pneumatic convective device contained therein; and the method further comprises applying heat to the patient through the first pneumatic convective device via the convective warming unit for at least 10 minutes.

55. The method of embodiment 54, wherein changing the warming device comprises removing the second pneumatic convective device from the pocket of the warming device, wherein the second configuration of the warming device comprises no second pneumatic convective device in the pocket;

wherein the pneumatic convective device is the second pneumatic convective device.

56. The method of embodiment 53, wherein the first configuration of the warming device is worn by the patient with the fastening devices secured.

57. The method of embodiment 56, wherein the second configuration of the warming device is the fastening devices unfastened.

58. The method of embodiment 56, wherein the second configuration of the warming device is a releasably attached pneumatic convective device being removed from the warming device and deployed onto a patient.

59. The method of embodiment 56, further comprising:

removing the warming device from the patient during the operative period.

60. The method of embodiment 58, further comprising:

covering the patient with the warming device in the second location; and applying convective heat through the first pneumatic convective device of the warming device in a third location.

What is claimed is:

1. A warming system, comprising:

a clinical garment comprising an inner surface to face a patient and an outer surface opposite the inner surface, wherein the clinical garment defines a flap;

a pneumatic convective layer coupled to the inner surface and including an inlet port aligned with the flap; and an insulative layer coupled to the clinical garment and encapsulated between the inner surface of the clinical garment and the pneumatic convective layer, wherein a cavity is defined between the pneumatic convective layer and the inner surface of the clinical garment, wherein the insulative layer is disposed in the cavity, wherein the insulative layer is directly contactable with the pneumatic convective layer, and wherein the insulative layer defines an opening aligned with the flap and the inlet port, thereby allowing an air hose of a warming unit to access the inlet port via the flap and the opening.

2. The warming system of claim 1, wherein the insulative layer comprises an insulative edge portion that is covered by the pneumatic convective layer, and wherein the insulative edge portion is configured to make the warming system non-linting.

3. The warming system of claim 1, wherein the pneumatic convective layer and the clinical garment are sealed together to form a sealed portion, wherein the insulative edge portion does not contact the sealed portion.

4. The warming device system of claim 2, wherein the insulative edge portion is treated by heat sealing, coating, or taping, or combinations thereof.

5. The warming system of claim 1, wherein the insulative layer has an R-value of between 0.5 and 3 R, inclusive.

6. The warming system of claim 1, wherein the clinical garment has a first garment surface area and the insulative layer has a second surface area that is at least 15% of the first garment surface area.

7. The warming system of claim 1, wherein the insulative layer comprises nonwoven fibers and has a weight of between 20 g/m2 and 210 g/m2, and a thickness between 0.1 cm and 2.1 cm.

8. The warming system of claim 1, wherein the insulative layer is a synthetic fiber thermal insulation comprising fibers that are less than 20 microns in average diameter, wherein the synthetic fiber thermal insulation comprises polyolefin fibers, polyester fiber, or polyimide fibers.

9. The warming system of claim 1, wherein the pneumatic convective layer comprises a first layer comprised of a synthetic material, and wherein the warming system further comprises a second layer coupled to the first layer and comprised of a nonwoven material.

10. The warming system of claim 9, wherein the insulative layer contacts the second layer and is disposed between the second layer and the inner surface of the clinical garment.

11. The warming system of claim 1, wherein the clinical garment has a reflective layer disposed thereon.

12. A system comprising:

the warming system of claim 1;

the warming unit; and the air hose configured to mate with the inlet port of the pneumatic convective layer.

13. A method comprising:

providing the system of claim 12 to a patient;

allowing the patient to wear the warming system in a first configuration before anesthesia during a preoperative period and in a first location;

changing the warming system to a second configuration before a patient receives anesthesia at a second location; and applying heat via the pneumatic convective layer to the patient during an operative period at the second location.

14. The method of claim 13, wherein:

in the first configuration, the pneumatic convective layer is coupled to the clinical garment and;

in the second configuration, the pneumatic convective layer is removed from the clinical garment and deployed onto a patient.

15. The warming system of claim 1, wherein the pneumatic convective layer comprises a first synthetic layer and the warming system further comprises a second synthetic layer, wherein the first and second synthetic layers define a cavity, and wherein the warming system further comprises first and second nonwoven layers coupled to the first and second synthetic layers, respectively.

16. The warming system of claim 15, wherein the insulative layer is sandwiched between the inner surface of the clinical garment and the second nonwoven layer.

17. The warming system of claim 1, wherein the pneumatic convective layer and the insulative layer are independently coupled to the clinical garment.

18. The warming system of claim 9, wherein the cavity is defined between the second layer and the inner surface of the clinical garment.

19. The warming system of claim 1, wherein the pneumatic convective layer comprises a single layer.

* * * * *